United States Patent [19]

Caponi

[11] Patent Number: 4,986,265
[45] Date of Patent: Jan. 22, 1991

[54] PROTECTIVE COVER FOR CAST

[76] Inventor: Ronald E. Caponi, P.O. Box 409, Orlando, Fla. 32802

[21] Appl. No.: 363,202

[22] Filed: Jun. 8, 1989

Related U.S. Application Data

[63] Continuation-in-part of Ser. No. 155,740, Feb. 16, 1988, abandoned.

[51] Int. Cl.⁵ .............................................. A61F 15/00
[52] U.S. Cl. ..................................... 128/82; 128/165; 128/846
[58] Field of Search ................... 128/82, 83, 155, 165, 128/846, 856, 878

[56] References Cited

U.S. PATENT DOCUMENTS

| | | | |
|---|---|---|---|
| 2,229,575 | 1/1941 | Kaplan | 128/82 |
| 2,334,206 | 11/1943 | Knohl | 128/165 |
| 3,741,203 | 6/1973 | Liman | 128/82 |
| 4,036,220 | 7/1977 | Bellasalma | 128/82 |
| 4,139,003 | 2/1979 | Little et al. | 128/82 |
| 4,346,699 | 8/1982 | Little et al. | 128/82 |
| 4,363,317 | 12/1982 | Broucek | 128/82 |
| 4,423,722 | 1/1984 | Dickman | 128/165 X |
| 4,610,245 | 9/1986 | Biearman | 128/82 |
| 4,646,727 | 3/1987 | Chambers | 128/82 |
| 4,911,151 | 3/1990 | Rankin et al. | 128/82 |

Primary Examiner—Robert A. Hafer
Assistant Examiner—Kevin G. Rooney
Attorney, Agent, or Firm—William M. Hobby, III

[57] ABSTRACT

A protective cover for covering a plaster cast, or the like on a patient, includes an elongated waterproof, flexible, polymer bag having an opening in one end thereof. The open end of the polymer bag has an elastic edge therearound to hold the elongated, waterproof, flexible, polymer bag over a cast on a patient's limb. A small piece of hook and loop material is attached to the flexible bag. An elongated, substantially flat sealing band is made of an elastic, resilient, waterproof foamed polymer material and has hook and loop material attached thereto with the hook material positioned at predetermined positions on one side of the flat sealing band and the other side of the sealing band being covered with a loop. The elongated, waterproof, flexible, polymer bag can be placed over a cast and the elongated, substantially flat sealing band attached on one end to the piece of hook and loop material on the bag and then wrapped around the open end thereof with a multiple, overlapping, ceiled wrap to seal the open end against the intrusion of liquid when the sealing band is stretched for a tight seal and attached with the hook and loop material.

4 Claims, 1 Drawing Sheet

PROTECTIVE COVER FOR CAST

This application is a continuation in part of application Ser. No. 07/155,740 filed Feb. 16, 1988 and now ABANDONED.

BACKGROUND OF THE INVENTION

The present invention relates to a protective cover for covering a cast and especially to such a cover having an elastic edge on a polymer bag and a separate flat sealing band which is stretched therearound a plurality of coiled wraps for a better seal.

It is well known that the plaster generally used to form a cast around broken or severely injured limbs and joints becomes soft and deteriorates when it gets wet. A patient is therefore required to make every effort to keep the cast dry at all times. A common practice with a patient having a cast has been to cover the outside surface of the cast with a sheet of plastic in an attempt to prevent water from reaching the surface of the plaster. This arrangement requires a seal of some kind around the upper portion of the cast bound limb to prevent water from leaking between the limp and the plaster and thereby coming into contact with the plaster cast. Homemade plastic seals of this type which generally resulted in a tight seal which is tight enough to prevent water leakage, results in a tourniquet and the blood supply to the injured limb being cut off or dangerously curtailed. If the seal is loosened, water leakage then occurs. The present invention is directed towards a waterproof covering for a cast bound limb having a sealing arrangement which effectively prevents water from contacting the plaster cast while at the same time having little or no affect on the circulation of the blood to the injured limb.

There have been quite a few suggestions in prior U.S. patents for covering a cast and sealing the cover for the cast to prevent intrusion of water into the cast. Typical prior patents can be seen in the MacKay U.S. Pat. No. 3,735,759, for a protective cover for a plaster cast and in the Little, et al, U.S. Pat. No. 4,139,003, for a waterproof cast protector. In the Lipson U.S. Pat. No. 3,785,374, a sealable container for liquid flotation of cast-bound limbs is provided, while the Scott U.S. Pat. No. 4,098,268, has a water impervious cover for an arm cast or a leg cast and uses a VELCRO seal with an inflatable cast cover. In the Metelnick U.S. Pat. No. 4,224,935, a bag protector for a light cast has a foot support and leg seal, while the Goldman, et al., U.S. Pat. No. 3,747,125, has a cast sheath for sealing a closure around the plaster cast. The Cook, Jr. U.S. Pat. No. 3,906,941, has a wrap around sealing method provided for a plastic bag placed around a cast.

In contrast to these prior art devices the present invention provides a cast cover of a thin polymer material having an elastic edge to hold the bag in place and a foam polymer seal which is resilient and elastic for stretching around the elastic edge of the polymer cover to provide a complete waterproof seal when attached with hook and loop material.

SUMMARY OF THE INvENTION

A protective cover for covering a cast on a patient is providing having and elongated, waterproof, flexible, polymer bag with an opening on at least one end thereof and the opening having an elastic edge formed thereon to hold the elongated, waterproof, flexible, polymer bag over a cast on a patient. The flexible bag has a small piece of hook and loop material attached adjacent the open end thereof. An elongated, substantially flat sealing band is made of an elastic resilient, waterproof foamed polymer material having hook and loop material attached thereto with the hook material positioned at predetermined positions on one side of the flat sealing band and the loop material covering the other side of the flat sealing band. This allows the elongated, waterproof, flexible, polymer bag to be placed over the cast and held in position with the elastic edge and the elongated, substantially flat, sealing band to be attached to the small piece of hook and loop material on the bag and then wrapped in a coiled overlapped fashion around the open end thereof to seal the open end against the patient's limp to prevent the intrusion of liquid. The hook material may be placed in a plurality of transverse strips on one side of the elongated, substantially flat, sealing band while the loop material may cover the other side of the elongated, substantially flat, sealing band.

BRIEF DESCRIPTION OF THE DRAWINGS

Other objects, features and advantages of the present invention will be apparent from the written description and the drawings in which.

Figure 1:
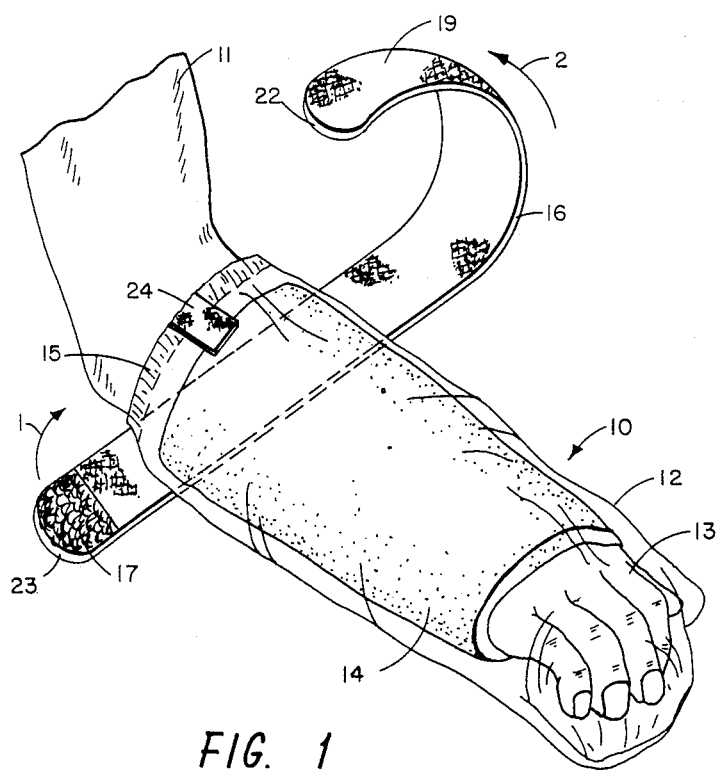
FIG. 1 is a perspective view of a protective cover for covering a cast on a patient in accordance with the present invention.
Figure 2:
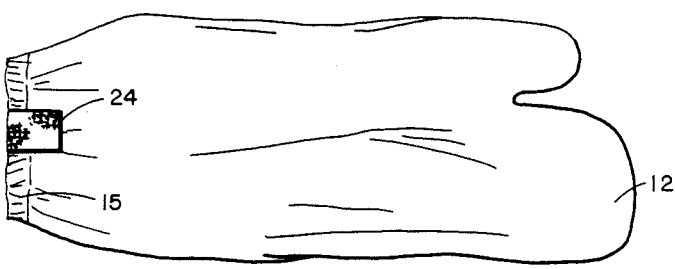
FIG. 2 is a side elevation of a polymer bag in accordance with the cast cover of FIG. 1.

3 is a side elevation of the sealing band used in FIG. 1; and

Figure 4:
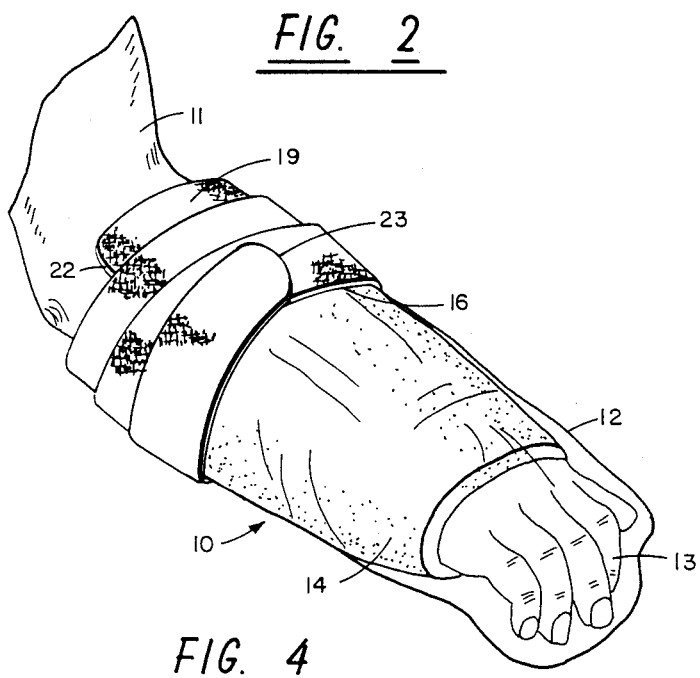
Figure 3:
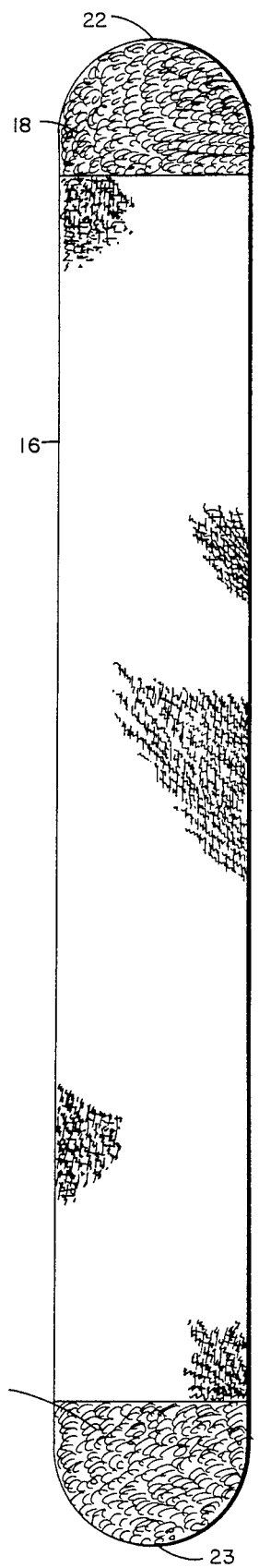

FIG. 4 is a perspective view in accordance with FIG. 1 having a cast cover sealed on a patient.

DESCRIPTION OF THE PREFERRED EMBODIMENT

Referring to FIGS. 1 through 4 of the drawings, a protective cover for covering a cast 10 is shown being place on a patient's arm in FIG. 1 and includes an elongated, waterproof, flexible, polymer bag 12 placed over the patient's hand 13 and cast 14 and having an annular elastic edge 15 on the open end thereof. The bag 12 can then be slipped over the cast and is held in place by the elastic edge 15 which also assist in sealing the bag. The polymer bag 12 has a small piece of VELCRO or hook and loop material 24 attached thereto. An elongated, substantially flat, sealing band 16 is made of an elastic, resilient, waterproof foamed polymer material, such as used in wet suits by scuba divers, and has hook material 17 attached to one end 22 thereof on one side thereof and hook material 18 attached to the other end 23 of the elongated strip 16.

Thus, when the elongated polymer band 16 is wrapped around the patient's limb 11 over the edge 15 of the bag 12, as shown in FIG. 1, the VELCRO end 17 or 18 can first be hooked to the VELCRO piece 24 and then pulled to stretch the foam band 16 in a multiple overlapping coiled wrap for connecting the hook and loop material 17 or 18 to the loop material 19 on the other side of band 16 to form a complete seal as shown in FIG. 4. The key to a good seal is a partial preliminary seal of the elastic edge 15 and then using the elastic, resilient foam material in the band 16 which can be stretched in multiple overlapping wraps over the edge 15 and compresses on the arm without causing a tourniquet affect, to provide a complete seal. The small piece of VELCRO 24 allows the user to attach one end of the band 16 so that a person can attach the cover without assistance from another person. The end strips 17 and 18 are hook material while the side 19 may be loop material.

A complete waterproof seal requires a preliminary elastic edge 15, as well as a band 16 made of a waterproof foamed polymer material which is both elastic and resilient and used with plural overlapping wraps and slightly stretched to obtain a complete seal. The cast protective cover in accordance with this invention is inexpensive to make and fully protects the cast of the patient. It is also easy to attach by a patient connecting one end of the band 16 VELCRO 17 to the VELCRO tab 24 to hold one end while the patient wraps and stretches the band 16 and attaches the VELCRO 18 to the loop side 19 of the band 16. It should however be cleared at this point that the present invention is not to considered limited to the forms shown which are to be considered illustrative rather than restrictive.

I claim:

1. A protective cover for covering a cast on a patient comprising:

an elongated, waterproof, flexible, polymer bag having an opening on at least one end thereof, said open end having an elastic edge formed thereon to hold said elongated, waterproof, flexible, polymer bag over a cast on a patient and said elongated flexible polymer bag having a piece of hook and loop material attached thereto;

an elongated, substantially flat, sealing band, said elongated, substantially flat sealing band being made of an elastic, resilient, waterproof foamed polymer material having hook and loop material attached thereto with the hook material positioned at predetermined positions on one side of said flat sealing band and the loop material covering a substantial portion of the other side of the flat sealing band and said elongated substantially flat sealing band being long enough to form a plurality of overlapping loops around a patient's limb; whereby said elongated, waterproof, flexible, polymer bag can be placed over a cast and the said elongated, substantially flat, sealing band wrapped around the open end thereof to seal the open end against the intrusion of liquid, said elongated, substantially flat sealing band being held in stretched position by the hook and loop material.

2. A protective cover for covering a cast on a patient in accordance with claim 1 in which said hook material is placed on each end of one side of said elongated, substantially flat, sealing band.

3. A protective cover for covering a cast on a patient in accordance with claim 2 in which said loop material covers the other side of said elongated, substantially flat, sealing band.

4. A protective cover for covering a cast on a patient in accordance with claim 3 in which said elongated, waterproof, flexible, polymer bag elastic edge has an annular elastic member formed in the elongated, waterproof, flexible, polymer bag edge.

* * * * *